United States Patent
Janardhan et al.

(10) Patent No.: US 12,290,631 B2
(45) Date of Patent: May 6, 2025

(54) ELECTRONIC SMOKING ARTICLE

(71) Applicant: Altria Client Services LLC, Richmond, VA (US)

(72) Inventors: Srinivasan Janardhan, Glen Allen, VA (US); Georgios D. Karles, Richmond, VA (US); Yezdi B. Pithawalla, Midlothian, VA (US); Gerd Kobal, Sandy Hook, VA (US); San Li, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 1047 days.

(21) Appl. No.: 14/332,785

(22) Filed: Jul. 16, 2014

(65) Prior Publication Data

US 2015/0020822 A1 Jan. 22, 2015

Related U.S. Application Data

(60) Provisional application No. 61/856,280, filed on Jul. 19, 2013.

(51) Int. Cl.
| | |
|---|---|
| A24F 40/48 | (2020.01) |
| A24F 40/485 | (2020.01) |
| A61M 11/04 | (2006.01) |
| A61M 15/06 | (2006.01) |
| A24F 40/10 | (2020.01) |
| A24F 40/42 | (2020.01) |

(52) U.S. Cl.
CPC .............. *A61M 15/06* (2013.01); *A24F 40/48* (2020.01); *A24F 40/485* (2020.01); *A61M 11/042* (2014.02); *A24F 40/10* (2020.01); *A24F 40/42* (2020.01); *A61M 2205/3606* (2013.01); *A61M 2205/8206* (2013.01); *A61M 2206/14* (2013.01)

(58) Field of Classification Search
CPC .... A24F 47/008; A24F 47/002; A24F 47/004; A24F 47/00; A61M 15/06
USPC .......................................... 131/209, 217, 195
See application file for complete search history.

(56) References Cited

U.S. PATENT DOCUMENTS

| | | |
|---|---|---|
| 4,135,523 A | 1/1979 | Luke et al. |
| 4,945,929 A | 8/1990 | Egilmex |

(Continued)

FOREIGN PATENT DOCUMENTS

| | | | | |
|---|---|---|---|---|
| EP | 2599514 A1 | * | 6/2013 | .......... A61M 11/041 |
| KR | 200454110 Y1 | | 6/2011 | |

(Continued)

OTHER PUBLICATIONS

Storz, Markus, "Machine translation of EP 2599514," Translated Jul. 1, 2021, Espacenet.com. (Year: 2021).*

(Continued)

*Primary Examiner* — Philip Y Louie
*Assistant Examiner* — Sonny V Nguyen
(74) *Attorney, Agent, or Firm* — Harness, Dickey & Pierce, P.L.C.

(57) ABSTRACT

An electronic smoking article includes a reservoir including a liquid aerosol formulation, a heater operable to at least partially volatilize the liquid aerosol formulation and form an aerosol and a spiral path insert including a channel having a spiral configuration along an outer periphery of the spiral path insert. A coating can be applied to the outer periphery of the spiral path insert.

21 Claims, 3 Drawing Sheets

(56) References Cited

U.S. PATENT DOCUMENTS

| | | | | |
|---|---|---|---|---|
| 5,309,900 A * | 5/1994 | Knoch | ............... | A61M 15/0086 |
| | | | | 128/200.14 |
| 5,591,334 A * | 1/1997 | Shimizu | ................ | A61M 15/02 |
| | | | | 210/243 |
| 5,630,409 A * | 5/1997 | Bono | ..................... | A61M 11/06 |
| | | | | 128/200.14 |
| 5,924,417 A | 7/1999 | Braithwaite et al. | | |
| 7,845,359 B2 | 12/2010 | Montaser | | |
| 7,878,963 B2 * | 2/2011 | Li | .......................... | A24D 3/045 |
| | | | | 131/331 |
| 8,127,772 B2 | 3/2012 | Montaser | | |
| 8,869,792 B1 * | 10/2014 | Lee | ....................... | A61M 15/06 |
| | | | | 128/202.21 |
| 2005/0045198 A1 | 3/2005 | Larson et al. | | |
| 2007/0062548 A1 * | 3/2007 | Horstmann | ............ | A24F 42/60 |
| | | | | 131/270 |
| 2007/0267032 A1 | 11/2007 | Shan | | |
| 2011/0094523 A1 * | 4/2011 | Thorens | ................ | A24F 47/008 |
| | | | | 131/194 |
| 2011/0290267 A1 * | 12/2011 | Yamada | ................... | A24F 42/60 |
| | | | | 131/329 |
| 2012/0144556 A1 * | 6/2012 | Fiebel | .................. | A61M 15/085 |
| | | | | 2/206 |
| 2012/0318882 A1 * | 12/2012 | Abehasera | ............ | A24F 47/008 |
| | | | | 239/1 |
| 2013/0056012 A1 * | 3/2013 | Hearn | ................... | A61M 15/06 |
| | | | | 131/273 |
| 2013/0074842 A1 | 3/2013 | Boucher et al. | | |
| 2013/0142868 A1 * | 6/2013 | Hoekman | ............ | A61M 15/009 |
| | | | | 424/450 |
| 2013/0192615 A1 * | 8/2013 | Tucker | ................... | H01C 17/00 |
| | | | | 131/328 |
| 2014/0261492 A1 | 9/2014 | Kane et al. | | |
| 2014/0283824 A1 * | 9/2014 | Wheelock | ............ | A61M 11/041 |
| | | | | 128/202.21 |
| 2015/0027477 A1 * | 1/2015 | Yoshino | ................ | A24F 47/008 |
| | | | | 131/337 |
| 2015/0181928 A1 * | 7/2015 | Liu | ........................ | A24F 47/008 |
| | | | | 131/329 |
| 2015/0305406 A1 * | 10/2015 | Li | .......................... | A24F 47/008 |
| | | | | 131/329 |
| 2016/0007648 A1 * | 1/2016 | Sutton | .................... | A24F 13/02 |
| | | | | 131/187 |
| 2017/0164653 A1 * | 6/2017 | Chen | ..................... | A24F 47/004 |
| 2017/0368273 A1 * | 12/2017 | Rubin | ................... | A61M 11/042 |

FOREIGN PATENT DOCUMENTS

| | | |
|---|---|---|
| WO | WO-98/08436 | 3/1998 |
| WO | WO-9823171 A1 | 6/1998 |
| WO | WO-2012026963 A2 * | 3/2012 .......... A61M 11/041 |

OTHER PUBLICATIONS

International Search Report and Written Opinion dated Nov. 26, 2014.

* cited by examiner

ELECTRONIC SMOKING ARTICLE

CROSS-REFERENCE TO RELATED APPLICATION

This application claims priority under 35 U.S.C. § 119(e) to U.S. provisional Application No. 61/856,280, filed on Jul. 19, 2013, the entire content of which is incorporated herein by reference thereto.

WORKING ENVIRONMENT

Many of the embodiments disclosed herein comprise electronic smoking articles, such as electronic cigarettes, operable to deliver liquid from a liquid supply source to a heater. The heater volatilizes a liquid to form an aerosol.

SUMMARY OF SELECTED FEATURES

An electronic smoking article operable to produce an aerosol includes a liquid supply (or reservoir) including a liquid aerosol formulation; a heater operable to at least partially volatilize the liquid aerosol formulation and form an aerosol; and a spiral path insert (SPI) located downstream of the heater and including at least one channel in an outer periphery of a body of the SPI. The at least one channel has a spiral configuration, an inlet at an upstream end of the channel, and an outlet at a downstream end of the channel through which aerosol produced by the heater travels before exiting the electronic smoking article.

DETAILED DESCRIPTION

An electronic smoking article includes a reservoir containing a liquid aerosol formulation. The liquid aerosol formulation is delivered to a heater where the liquid aerosol formulation is heated, volatilized, and forms an aerosol. As used herein, the term "electronic smoking article" is inclusive of all types of electronic smoking articles, regardless of form, size or shape, including electronic cigarettes, electronic cigars, electronic pipes, electronic hookahs and the like. The liquid aerosol formulation can include nicotine or be nicotine free. Moreover, the liquid aerosol formulation can include tobacco flavors or instead, or in combination include other suitable flavors.

Preferably, the aerosol passes through a spiral path insert (SPI) after formation and prior to passing through a mouth end insert so as to cool the aerosol by forcing the aerosol to travel along a longer path. As the aerosol passes along the spiral path of the SPI, heat transfers from the aerosol to the SPI also occurs to further reduce the temperature of the aerosol. The SPI also increases the residence time of the aerosol within the electronic smoking article. The residence time can be adjusted (increased or decreased) by lengthening or shortening the spiral path or paths along a periphery of the SPI.

Figure 1:
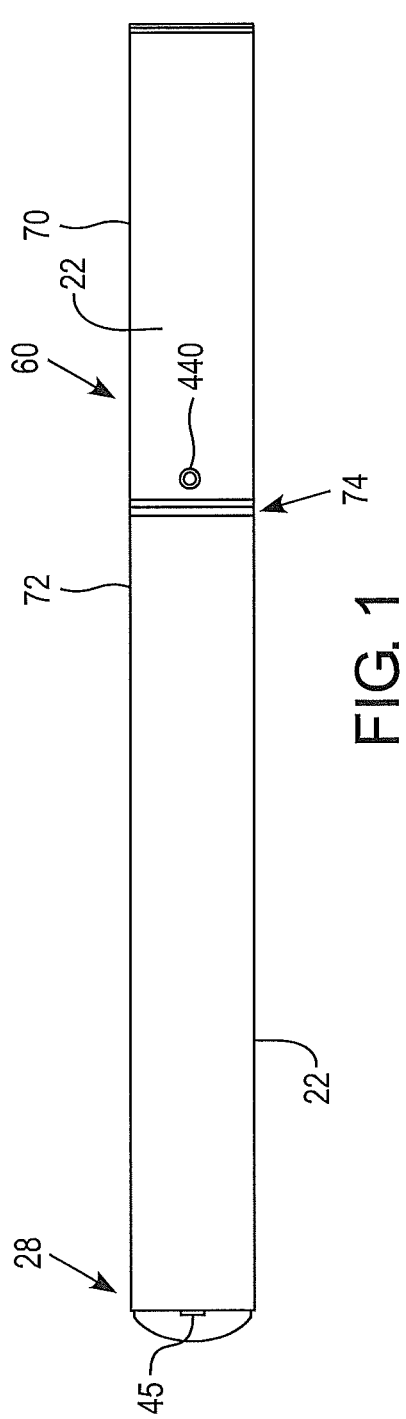
FIG. 1 is a side view of an electronic smoking article constructed according to the teachings herein.
Figure 2:
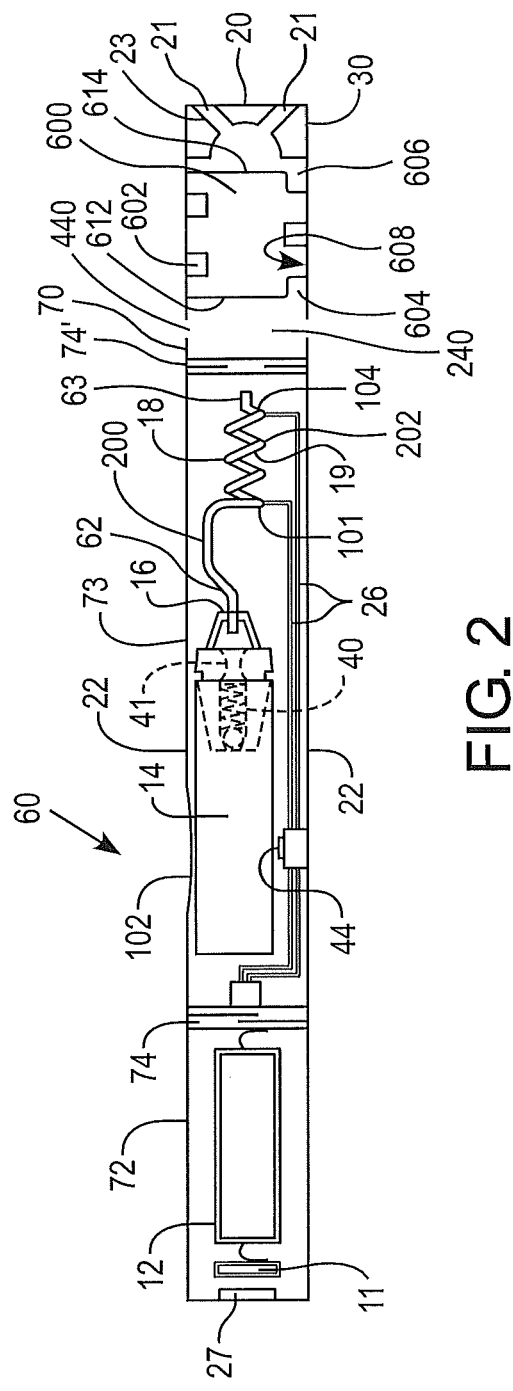
FIG. 2 is a cross-sectional view of an electronic smoking article according to a first embodiment.
Figure 3:
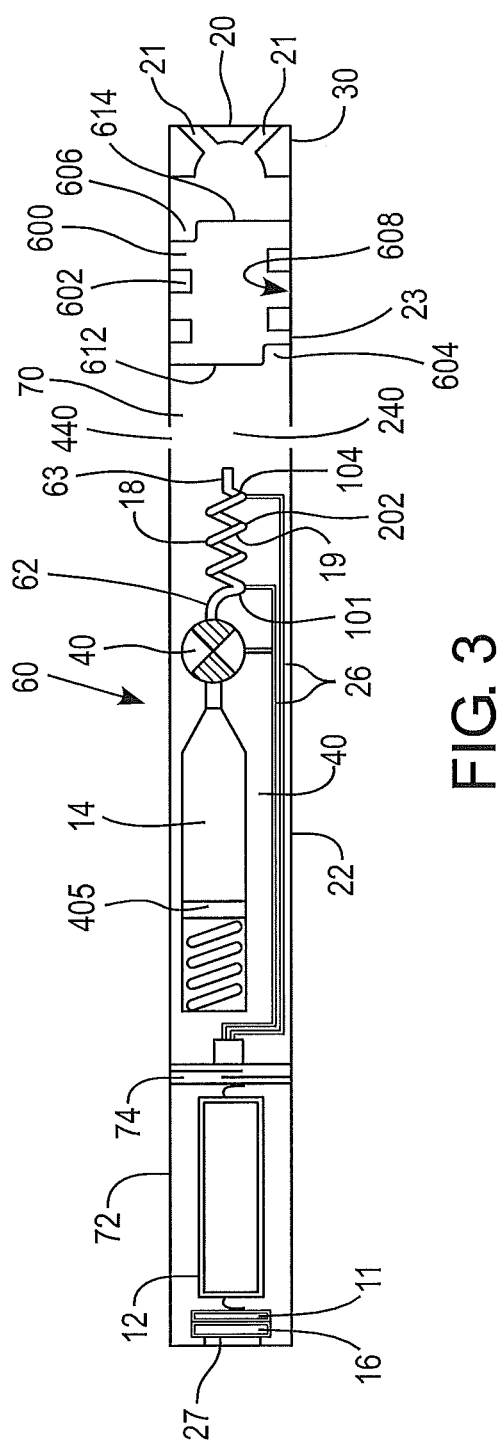
FIG. 3 is a cross-sectional view of another embodiment of an electronic smoking article according to a second embodiment.
Figure 4:
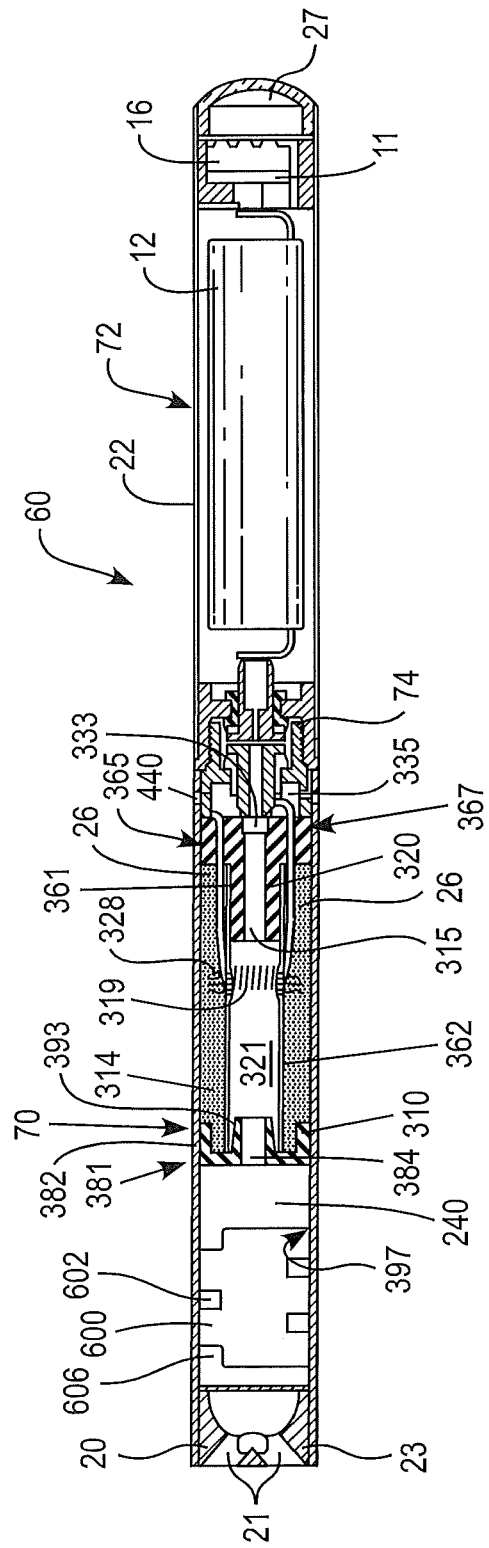
FIG. 4 is a cross-sectional view of an electronic smoking article according to a third embodiment.

Preferably, an SPI 600 is located downstream of a heater in an electronic smoking article 60 as shown in greater detail in FIGS. 2, 3, and 4. As shown in FIG. 1, the electronic smoking article 60 comprises a replaceable cartridge (or first section) 70 and a reusable fixture (or second section) 72, which are coupled together at a threaded joint 74 or by other convenience such as a snug-fit, snap-fit, detent, clamp and/or clasp. In some embodiments, the electronic smoking article is constructed from a single, unitary outer casing, in which case the threaded joint 74 is omitted.

As shown in FIG. 3, the first section 70 can house a mouth-end insert 20, a capillary aerosol generator including a capillary (capillary tube) 18, a heater 19 to heat at least a portion of the capillary 18, a reservoir 14 and optionally a valve 40. Alternatively, as shown in FIG. 4, the first section 70 can house a mouth end insert 20, a heater 319, a flexible, filamentary wick 328 and a reservoir 314 as discussed in further detail below.

The second section 72 can house a power supply 12 (shown in FIGS. 2, 3 and 4), control circuitry 11, and optionally a puff sensor 16 (shown in FIGS. 3 and 4). The threaded portion 74 of the second section 72 can be connected to a battery charger when not connected to the first section 70 for use so as to charge the battery.

As shown in FIG. 2, the electronic smoking article 60 can also include a middle section (third section) 73, which can house the reservoir 14, heater 19 and valve 40. The middle section 73 can be adapted to be fitted with a threaded joint 74' at an upstream end of the first section 70 and a threaded joint 74 at a downstream end of the second section 72. In this embodiment, the first section 70 houses the mouth-end insert 20, while the second section 72 houses the power supply 12 and control circuitry.

Preferably, the first section 70, the second section 72 and the optional third section 73 include an outer cylindrical housing 22 extending in a longitudinal direction along the length of the electronic smoking article 60. Moreover, in one embodiment, the middle section 73 is disposable and the first section 70 and/or second section 72 are reusable. In another embodiment, the first section 70 can also be replaceable so as to avoid the need for cleaning the capillary 18 and/or heater 19. The sections 70, 72, 73 can be attached by threaded connections whereby the middle section 73 can be replaced when the reservoir 14 is used up.

As shown in FIG. 2, the outer cylindrical housing 22 can include a cutout or depression 102 which allows a smoker to manually apply pressure to the reservoir 14. Preferably, the outer cylindrical housing 22 is flexible and/or compressible along the length thereof and fully or partially covers the reservoir 14. The cutout or depression 102 can extend partially about the circumference of the outer cylindrical housing 22. Moreover, the reservoir 14 is compressible such that when pressure is applied to the, liquid is pumped from the reservoir 14 to the capillary 18. A pressure activated switch 44 can be positioned beneath the reservoir 14. When pressure is applied to the reservoir 14 to pump liquid, the switch is also pressed and a heater 19 is activated. The heater 19 can be a portion of the capillary 18.

In the preferred embodiment, the reservoir 14 is a tubular, elongate body formed of an elastomeric material so as to be flexible and/or compressible when squeezed. Preferably, the elastomeric material can be selected from the group consisting of silicone, plastic, rubber, latex, and combinations thereof.

Preferably, the compressible reservoir 14 has an outlet 16 which is in fluid communication with a capillary 18 so that when squeezed, the reservoir 14 can deliver a volume of liquid material to the capillary 18. Simultaneous to delivering liquid to the capillary, the power supply 12 is activated upon application of manual pressure to the pressure switch and the capillary 18 is heated to form a heated section wherein the liquid material is volatilized. Upon discharge from the heated capillary 18, the volatilized material expands, mixes with air and forms an aerosol.

Preferably, the reservoir 14 extends longitudinally within the outer cylindrical housing 22 of the first section 70 (shown in FIGS. 3 and 4) or the middle section 73 (shown in FIG. 2). Moreover, the reservoir 14 comprises a liquid aerosol formulation which is volatilized when heated and forms an aerosol when discharged from the capillary 18.

In the embodiments shown in FIGS. 2 and 3, the capillary 18 includes an inlet end 62 in fluid communication with the outlet 16 of the reservoir 14, and an outlet end 63 operable to expel volatilized liquid material from the capillary 18. In a preferred embodiment, as shown in FIGS. 2 and 3, the reservoir 14 may include a valve 40.

As shown in FIG. 2, the valve 40 can be a check valve that is operable to maintain the liquid material within the, but opens when the reservoir 14 is squeezed and pressure is applied. Preferably, the check valve 40 opens when a critical, minimum pressure is reached so as to avoid inadvertent dispensing of liquid material from the reservoir 14 or activating the heater 19. Once pressure upon the reservoir 14 is relieved, the valve 40 closes. The heated capillary 18 discharges liquid remaining downstream of the valve 40.

As shown in FIG. 3, in other embodiments, the valve 40 can be a two-way valve and the reservoir 14 can be pressurized. For example, the reservoir 14 can be pressurized using a pressurization arrangement 405 which applies constant pressure to the reservoir 14. For example, pressure can be applied to the reservoir 14 using an internal or external spring and plate arrangement which constantly applies pressure to the reservoir 14. Alternatively, the reservoir 14 can be compressible and positioned between two plates that are connected by springs or the reservoir 14 could be compressible and positioned between the outer housing and a plate that are connected by a spring so that the plate applies pressure to the reservoir 14.

Preferably, the capillary 18 of FIGS. 2 and 3 has an internal diameter of 0.01 to 10 mm, preferably 0.05 to 1 mm, and more preferably 0.05 to 0.4 mm. Also preferably, the capillary 18 may have a length of about 5 mm to about 72 mm, more preferably about 10 mm to about 60 mm or about 20 mm to about 50 mm. In one embodiment, the capillary 18 is substantially straight. In other embodiments, the capillary 18 is coiled and/or includes one or more bends therein to conserve space and/or accommodate a long capillary.

In these embodiments, the capillary 18 is formed of a conductive material, and thus acts as its own heater 19 by passing current through the capillary. The capillary 18 may be any electrically conductive material capable of being resistively heated, while retaining the necessary structural integrity at the operating temperatures experienced by the capillary 18, and which is non-reactive with the liquid material. Suitable materials for forming the capillary 18 are selected from the group consisting of stainless steel, copper, copper alloys, porous ceramic materials coated with film resistive material, Inconel® available from Special Metals Corporation, which is a nickel-chromium alloy, nichrome, which is also a nickel-chromium alloy, and combinations thereof.

Alternatively, the capillary 18 may be a non-metallic tube such as, for example, a glass tube having a conductive material capable of being resistively heated, such as, for example, stainless steel, nichrome or platinum wire, arranged there along.

Preferably, at least two electrical leads 26 are bonded to a metallic capillary 18 by brazing or crimping. Preferably, one electrical lead 26 is attached to a first, upstream portion 101 of the capillary 18 and a second electrical lead 26 is attached to a downstream, end portion 104 of the capillary 18, as shown in FIGS. 2 and 3. By passing an electrical current through the capillary 18, the capillary 18 is heated and liquid material contained therein is volatilized.

Referring to FIG. 4, in an embodiment, an electronic smoking article 60 preferably comprises a heater 319, a filamentary wick 328, and an annular reservoir (liquid supply). The first section 70 includes an outer tube (or casing) 22 extending in a longitudinal direction and an inner tube (or chimney) 362 coaxially positioned within the outer tube 322. Preferably, the SPI 600 is positioned downstream of the inner tube 362. Also preferably, a nose portion 361 of an upstream gasket (or seal) 320 is fitted into an upstream end portion 365 of the inner tube 362, while at the same time, an outer perimeter 367 of the gasket 320 provides a liquid-tight seal with an interior surface 397 of the outer casing 22. The upstream gasket 320 also includes a central, longitudinal air passage 315, which opens into an interior of the inner tube 362 that defines a central channel 321. A transverse channel 333 at an upstream portion of the gasket 320 intersects and communicates with the central channel 315 of the gasket 320. This channel 333 assures communication between the central channel 315 and a space 335 defined between the gasket 320 and a threaded connection 74.

Preferably, a nose portion 393 of a downstream gasket 310 is fitted into a downstream end portion 381 of the inner tube 362. An outer perimeter 382 of the gasket 310 provides a substantially liquid-tight seal with an interior surface 397 of the outer casing 22. The downstream gasket 310 includes a central channel 384 disposed between the central passage 321 of the inner tube 362 and the mouth end insert 20.

In this embodiment, the reservoir 314 is contained in an annulus between an inner tube 362 and an outer casing 22 and between the upstream gasket 320 and the downstream gasket 310. Thus, the reservoir 314 at least partially surrounds the central air passage 321. The reservoir 314 comprises a liquid material and optionally a liquid storage medium (not shown) operable to store the liquid material therein.

The inner tube 362 has a central air passage 321 extending therethrough which houses the heater 319. The heater 319 is in contact with the filamentary wick 328, which preferably extends between opposing sections of the reservoir 314 so as to deliver the liquid aerosol formulation from the reservoir to the heater 319.

Preferably, the electronic smoking article 60 of each embodiment described herein also includes at least one air inlet 440. As shown in FIG. 4, the at least one air inlet 440 can be located upstream of the heater 319.

In the embodiments shown in FIGS. 2 and 3, the at least one air inlet 440 is preferably arranged downstream of the capillary 18 so as to minimize drawing air along the capillary and thereby avoid cooling of the capillary 18 during heating cycles.

The power supply 12 of each embodiment can include a battery arranged in the electronic smoking article 60. The power supply 12 is operable to apply voltage across the heater 19 associated with the capillary 18, as shown in FIGS. 2 and 3, or the heater 319 associated with the filamentary wick 328, as shown in FIG. 4. Thus, the heater 19, 319 volatilizes liquid material according to a power cycle of either a predetermined time period, such as a 2 to 10 second period.

The battery can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, preferably, the electronic smoking article 60 is usable by a smoker until the energy in the power supply is depleted. Alternatively, the power supply 12 may be rechargeable and include circuitry allowing the battery to be chargeable by an external charging device. The control circuitry 11 can be programmable and can include an application specific integrated circuit (ASIC). In other embodiments, the control circuitry 11 can include a microprocessor programmed to carry out functions such as heating the capillaries and/or operating the valves.

Preferably, the electronic smoking article 60 of each embodiment also includes control circuitry which can be on a printed circuit board 11 (shown in FIGS. 2, 3 and 4). The control circuitry 11 can also include a heater activation light 27 that is operable to glow when the heater 19, 319 is activated.

As shown in FIGS. 2, 3, and 4 the electronic smoking article 60 includes a spiral path insert (SPI) 600 at a location downstream of the heater 19, 319. In the preferred embodiment, as shown in FIGS. 2, 3, 4, 5 and 6 the SPI 600 includes at least one channel 602 in an outer periphery 608 of an impermeable body 610 of the SPI 600. Moreover, the SPI 600 remains in a fixed position within the electronic smoking article 60 during smoking. Preferably, the channel 602 has a spiral configuration. Moreover, the channel 602 has an inlet 604 at an upstream end 612 of the SPI 600 and an outlet 606 at a downstream end 614 of the SPI 600.

Preferably, the channel 602 includes at least two turns about the outer periphery 608 of the body 610 of the SPI 600. In one embodiment, the SPI 600 can include two spiral channels (not shown) having inlets at diametrically opposite ends of the SPI 600 such that aerosol can enter the channels at two different locations and crisscross along the SPI 600 as the aerosol travels.

Also preferably, the channel 602 has a variable width and a variable depth along a length of the SPI 600. In another embodiment, the channel 602 has a substantially uniform width and a substantially uniform depth along a length of the SPI 600.

Preferably, the SPI 600 is formed of an air impermeable material. In one embodiment, the SPI 600 is formed of at least one plastic selected from the group consisting of polyethylene, low density polyethylene, polyether ether ketone (PEEK) and combinations thereof. Alternatively, the SPI 600 can be formed of stainless steel.

In the preferred embodiment, the SPI 600 has a length ranging from about 2 mm to about 30 mm. Moreover, the SPI 600 has an outer diameter that is about the same as an inner diameter of the outer housing 22 of the electronic smoking article 60. Preferably, the at least one channel 602 has a width ranging from about 0.1 mm to about 2.0 mm and a depth ranging from about 0.01 mm to about 2.0 mm.

Since the SPI 600 is preferably air impermeable and the outer diameter of the SPI 600 is about the same as the inner diameter of the outer housing 22, aerosol is only able to pass from the heater to the mouth end insert 20 via the channel 602 formed in the outer periphery 608 of the SPI 600. Preferably, the channel 602 of the SPI 600 is designed such that the SPI 600 does not contribute any significant change to the overall resistance to draw (RTD) of the electronic smoking article 60.

During smoking, as aerosol travels along the channel 602, heat transfer occurs between the aerosol and the SPI 600. Since the channel 602 has a spiral configuration about the outer periphery 608 of the SPI 600, the aerosol must travel along a longer path as compared to aerosol travelling from a heater to a mouth end insert in an electronic smoking article lacking a SPI 600. Accordingly, the aerosol has a longer residence time between formation and delivery to the smoker which results in additional cooling of the aerosol prior to reaching the smoker. The average temperature in degrees Celsius per puff over 11 puffs for an electronic cigarette as shown in FIG. 4 including the SPI 600 as compared to an electronic cigarette as shown in FIG. 4, but lacking an SPI 600 is shown in Table 1 below.

TABLE 1

|  | Puff 1 | Puff 2 | Puff 3 | Puff 4 | Puff 5 | Puff 6 | Puff 7 | Puff 8 | Puff 9 | Puff 10 | Puff 11 | Average | Std. Dev. |
| --- | --- | --- | --- | --- | --- | --- | --- | --- | --- | --- | --- | --- | --- |
| Cartomizer without SPI | 58.1 | 58.4 | 57.2 | 57.2 | 55.9 | 57.4 | 58.7 | 59.7 | 58.4 | 58.2 | 59.1 | 58.0 | 1.0 |
| Cartomizer with SPI | 33.8 | 36.1 | 36.9 | 38.4 | 39.0 | 39.2 | 40.0 | 40.0 | 40.4 | 39.8 | 40.2 | 38.5 | 2.1 |

As shown in Table 1, the electronic smoking article 60 including the SPI 600 has a significant temperature reduction for all puffs as compared to a similar electronic smoking article lacking an SPI 600.

In a preferred embodiment, the SPI 600 can be formed of a plastic and have at least one additive extruded therewith. In another embodiment, the SPI 600 can include a coating along the channel 602 of the SPI 600. Preferably, the coating includes at least one additive selected from the group consisting of flavors, aerosol modifiers, aromatic materials, pH modifying agents, chemesthesis agents, and combinations thereof.

If the SPI 600 includes an additive, the additive is eluted into the aerosol as the aerosol passes along the channel 602. In one embodiment, the additives can be microencapsulated with water soluble materials having varying levels of water solubility so as to provide controlled release of the additive over a period of time. In another embodiment, the SPI 600 can be extruded with additives and include the coating. By including an additive-containing coating along with the additives in the SPI 600, release of the additives can be staggered during smoking and/or multiple additives can be delivered.

As used herein, the term "additive" means any material or component, which modifies the characteristics of the electronic smoking article 60 when the electronic smoking article 60 is smoked. Any appropriate additive material or combination of materials may be contained in or on the SPI 600. Such additive materials include flavor materials, aromatic materials, pH modifying agents, chemesthesis agents including cooling agents and warming agents, carbon dioxide formers, commercially available flavor systems, nicotine in liquid, salt or powder form, and other smoke modifiers.

As used herein, the term "flavor material" means any liquid or solid flavor containing material or formulation that can release flavors and/or aromas into the aerosol stream. Suitable flavors or flavorings include, but are not limited to, menthol, mint, such as peppermint and spearmint, chocolate, licorice, citrus and other fruit flavors, gamma octalactone, vanillin, ethyl vanillin, breath freshener flavors, spice flavors such as cinnamon, methyl salicylate, linalool, bergamot oil, geranium oil, lemon oil, ginger oil, and tobacco flavor. Other suitable flavors may include flavor compounds selected from the group consisting of an acid, an alcohol, an ester, an aldehyde, a ketone, a pyrazine, combinations or blends thereof and the like.

The flavor material can be in the form of particles, granules, fibers, capsules, microcapsules, powders, crushed plant material, aromatic barks, seeds, pieces of dried fruits and/or root material, or any other suitable form. For example, the flavor material can include tobacco beads, flavor beads, mentholated flavor beads, flavor capsules and other flavor materials as used in traditional tobacco smoke filters.

Suitable flavor materials can be non-volatile or volatile and can be delivered to the mouth via the condensation of the aerosol in the filter followed by entrapment and/or dissolution of the flavor material in droplets and/or deposition of the droplets to the tongue of the smoker during a puff. The droplets can consist of constituents used to form the aerosol including propylene glycol, glycerin, water and optionally nicotine. The flavor material can be released into the aerosol.

The flavor materials can provide a bitter taste. Suitable compounds which provide a bitter taste include, without limitation, caffeine, denatonium benzoate, theobromine, quinine, and naringin.

The flavor materials can provide a sour taste. Suitable compounds which provide a sour taste include, without limitation, citric acid, malic acid, succinic acid and tartaric acid. While not wishing to be bound by theory, the addition of an acid may also act to lower the pH of the aerosol and reduce harshness of the aerosol.

The flavor materials can provide a salty taste. Suitable compounds which provide a salty taste include, without limitation, sodium chloride and potassium chloride.

The flavor materials can provide a sweet taste. Suitable compounds which provide a sweet taste include, without limitation, carbohydrates, including sucrose, and high intensity sweeteners, including sucralose and saccharin.

The flavor materials can provide umami and mouth feel. Suitable compounds which provide umami and mouth feel include, without limitation, monosodium glutamate, gamma-glutamyl peptides, such as gamma-glutamycysteine-beta-alanine, (R)-strombine.

In one embodiment, the additive can be a chemesthesis agent and/or can be chosen to alter the mouthfeel of the aerosol. For example, the additive can be a chemesthesis agent that provides a warm, tingling sensation and/or a cooling sensation. Additives such as capsaicin, piperine, alpha-hydroxy-sanshool, and (8)-gingerole can be included to provide a warm, tingling or burning sensation. Additives including menthol, menthyl lactate, WS-3 (N-Ethyl-p-menthane-3-carboxamide), WS-23 (2-Isopropyl-N,2,3-trimethylbutyramide) and Evercool 180™ (available from Givaudan SA) can be included to provide a cooling sensation. In addition, the additive can include extracts, such as coffee extract, red pepper extract, ginger extract and peppermint oil.

Figure 5:
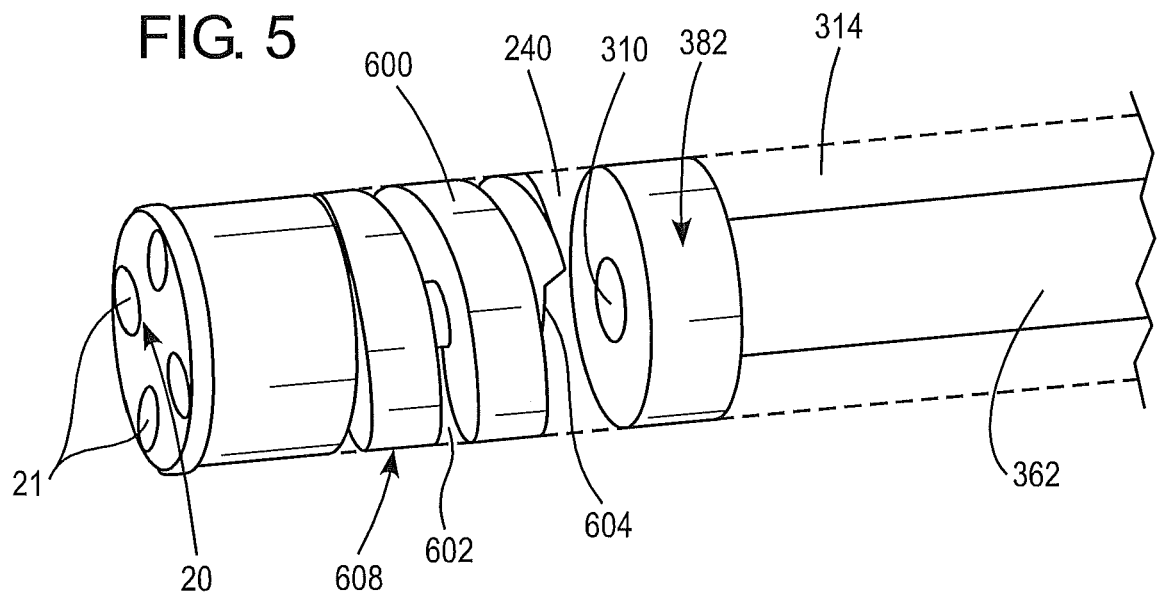
FIG. 5 is a partial, perspective view of an electronic smoking article including spiral path insert (SPI) and having a clear outer casing.
Figure 6:
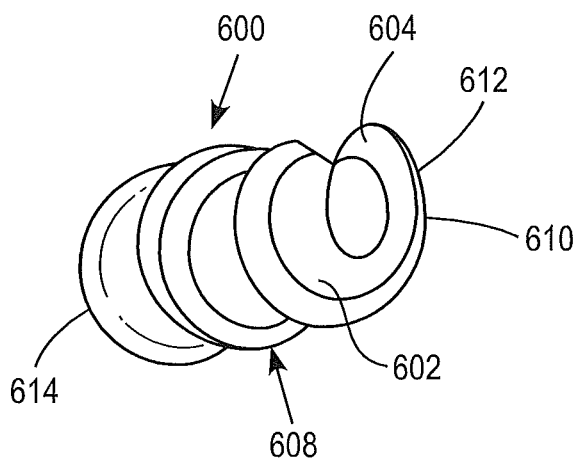
FIG. 6 is a perspective view of a SPI as described herein.

Preferably, the SPI 600 is located downstream of the heater 19, 319 so that minimum heat exposure is experienced by the additives. Thus, preferably, the SPI 600 is located so that the SPI 600 and/or additives contained therein are not exposed to temperatures above about 150° C. Moreover, as shown in FIGS. 4 and 5, preferably, the SPI 600 is located downstream of the inner tube 362. Also preferably, as shown in FIGS. 2, 3, 4 and 5, the electronic smoking article 60 includes a mixing chamber 240 that the aerosol must pass through before reaching the SPI 600.

As shown in FIGS. 2, 3, 4, and 5, the electronic smoking article 60 can further include the mouth-end insert 20 having at least two off-axis, preferably diverging outlets 21. Preferably, the mouth-end insert is located downstream of the tubular filter segment 600. In other embodiments (not shown) the tubular filter segment 600 can be downstream of the mouth-end insert 20.

Preferably, the mouth-end insert 20 includes at least two diverging outlets 21. (e.g, 3, 4, 5, or preferably 6 to 8 outlets or more). Preferably, the outlets 21 of the mouth-end insert 20 are located at ends of off-axis passages 23 and are angled outwardly in relation to the longitudinal direction of the electronic smoking article 60 (i.e., divergently). As used herein, the term "off-axis" denotes at an angle to the longitudinal direction of the electronic smoking article.

Preferably, the electronic smoking article 60 is about the same size as a conventional smoking article. In some embodiments, the electronic smoking article 60 can be about 80 mm to about 110 mm long, preferably about 80 mm to about 100 mm long and about 7 mm to about 8 mm in diameter. For example, in an embodiment, the electronic smoking article is about 84 mm long and has a diameter of about 7.8 mm.

The outer cylindrical housing 22 of the electronic smoking article 60 may be formed of any suitable material or combination of materials. Preferably, the outer cylindrical housing 22 is formed of metal and is part of the electrical circuit.

Preferably, the liquid aerosol formulation for use in each of the electronic smoking articles 60 described herein includes at least one aerosol former, water, and flavors.

In the preferred embodiment, the at least one aerosol former is selected from the group consisting of propylene glycol, glycerin and combinations thereof. Preferably, the at least one aerosol former is included in an amount ranging from about 40% by weight based on the weight of the liquid formulation to about 90% by weight based on the weight of the liquid formulation (e.g., about 50% to about 80%, about 55% to about 75% or about 60% to about 70%).

Preferably, the liquid formulation also includes water. Water can be included in an amount ranging from about 5% by weight based on the weight of the liquid formulation to about 20% by weight based on the weight of the liquid formulation, more preferably in an amount ranging from about 10% by weight based on the weight of the liquid formulation to about 15% by weight based on the weight of the liquid formulation.

The liquid aerosol formulation optionally includes at least one flavorant in an amount ranging from about 0.2% to about 15% by weight (e.g., about 1% to about 12%, about 2% to about 10%, or about 5% to about 8%). The at least one flavorant can be a natural flavorant or an artificial flavorant. Preferably, the at least one flavorant is selected from the group consisting of tobacco flavor, menthol, wintergreen, peppermint, herb flavors, fruit flavors, nut flavors, liquor flavors, and combinations thereof.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions. Although the inner and outer tubular structures of the embodiments described herein are preferably cylindrical, they can be instead square, rectangular, triangular, or oval in cross-section, or some other form.

It will now be apparent that a new, improved, and nonobvious electronic smoking article has been described in this specification with sufficient particularity as to be understood by one of ordinary skill in the art. Moreover, it will be apparent to those skilled in the art that numerous modifications, variations, substitutions, and equivalents exist for features of the electronic smoking article which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. An electronic article comprising:

a cartridge for containing a formulation and including a mouth-end portion;

a heater for at least partially volatizing the formulation;

a mixing chamber entirely downstream of the heater and upstream of the mouth-end portion;

a mouth-end insert in the mouth-end portion; and a spiral path insert (SPI), downstream of the mixing chamber, upstream of the mouth-end insert and defining a spiral channel, a spiral channel inlet, and a spiral channel outlet, the spiral path insert being impermeable, and the spiral channel being a closed spiral channel defined by the spiral path insert and an interior surface of an outer casing such that the closed spiral channel is the only path from the heater to the mouth-end insert wherein the SPI further defines the spiral channel as having a variable width and a variable depth along a length the spiral channel, the SPI including an additive within the SPI and being configured to be eluted into an aerosol, the additive being integral to the SPI.

2. The electronic article of claim 1, wherein the SPI further defines the spiral channel as having at least two turns about an outer periphery of the SPI.

3. The electronic article of claim 1, wherein the SPI comprises one material or a combination of materials selected from a group of materials including polyethylene, low density polyethylene, and polyether ether ketone (PEEK).

4. The electronic article of claim 1, wherein the SPI comprises a length ranging from about 2 mm to about 30 mm and an outer diameter that is about the same as an inner diameter of an outer housing of the electronic article.

5. The electronic article of claim 1, wherein the SPI further defines the spiral channel as having a width ranging from about 0.1 mm to about 2.0 mm and a depth ranging from about 0.01 mm to about 2.0 mm.

6. The electronic article of claim 1, further comprising:

a coating on the SPI, the coating comprising a coating additive.

7. The electronic article of claim 6, wherein the coating additive is one additive or a combination of additives selected from a group of additives including flavors, modifiers, aromatic materials, pH modifying agents, chemesthesis agents, and combinations thereof.

8. The electronic article of claim 1, the SPI further defining at least one additional spiral channel.

9. The electronic article of claim 1, wherein the spiral channel outlet is in fluid communication with the mouth end insert.

10. The electronic article of claim 1, further comprising:

a coating on the SPI, the coating comprising an additive;

wherein the additive is encapsulated or microencapsulated.

11. The electronic article of claim 1, wherein the heater comprises a capillary tube in fluid communication with the cartridge.

12. The electronic article of claim 11, wherein the cartridge is pressurized and comprises a mechanically or electrically operated valve at an outlet of the cartridge.

13. The electronic article of claim 11, wherein the cartridge is compressible such that the formulation is manually pumped to the capillary tube.

14. The electronic article of claim 1, wherein the cartridge further comprises, a formulation reservoir, and wherein the heater is a coil heater in communication with a filamentary wick that is provided to draw formulation from the reservoir via capillary action.

15. The electronic article of claim 14, wherein the electronic article further comprises:

an outer tube extending in a longitudinal direction;

an inner tube within the outer tube; and the cartridge comprising the formulation contained in an annulus between the outer tube and the inner tube, wherein the heater is located in the inner tube and the filamentary wick is in communication with the formulation reservoir and partially surrounded by the heater such that the filamentary wick delivers the formulation to the heater and the heater heats the formulation to a temperature sufficient to vaporize the formulation.

16. The electronic article of claim 15, the electronic article further comprising:

a second section comprising, a power supply configured to apply voltage across the heater.

17. The electronic article of claim 1, wherein the defined spiral channel includes a spiral axis along the airflow path within the electronic article.

18. The electronic article of claim 1, wherein the mixing chamber includes a gasket at an upstream end of the mixing chamber, the gasket having an opening at the center of the gasket between the mixing chamber and the heater.

19. The electronic article of claim 1, wherein the SPI is formed of a plastic, and the SPI is formed by extruding the plastic and additive together.

20. An electronic article comprising:
   a reservoir for containing a formulation;
   a heater for at least partially volatizing the formulation;
   a mixing chamber, entirely downstream of the heater, for promoting mixing of the at least partially volatized formulation with air;
   a mouth-end insert; and
   a spiral path insert (SPI) upstream of the mouth-end insert, downstream of the mixing chamber, and defining a spiral channel, a spiral channel inlet and a spiral channel outlet, the spiral path insert being impermeable, and the spiral channel being a closed spiral channel defined by the spiral path insert and an interior surface of an outer casing such that the closed spiral channel is the only path from the heater to the mouth-end insert, wherein the SPI further defines the spiral channel as having a variable width and a variable depth along a length the spiral channel, the SPI including an additive within the SPI and being configured to be eluted into an aerosol, the additive being integral to the SPI.

21. The electronic article of claim 20, wherein the defined spiral channel includes a spiral axis along the airflow path within the electronic article.

* * * * *